United States Patent [19]
Rinner

[11] Patent Number: 5,980,547
[45] Date of Patent: Nov. 9, 1999

[54] ROTARY CUTTER

[75] Inventor: James A. Rinner, Racine, Wis.

[73] Assignee: Beere Precision Medical Instruments, Inc., Racine, Wis.

[21] Appl. No.: 09/179,057

[22] Filed: Oct. 26, 1998

[51] Int. Cl.⁶ .................................................. A61B 17/32
[52] U.S. Cl. ............................................................. 606/180
[58] Field of Search ...................... 606/180, 170, 606/167, 171; 604/22

[56] References Cited

U.S. PATENT DOCUMENTS 5,766,199  6/1998  Heisler et al. .......................... 606/180
5,879,358  3/1999  Semm ...................................... 606/180
5,879,365  3/1999  Whitfield et al. ........................ 606/180

Primary Examiner—Michael Buiz
Assistant Examiner—Kevin Truong
Attorney, Agent, or Firm—Arthur J. Hansmann

[57] ABSTRACT

A rotary cutter having two telescopically related tubes with cutting edges on the distal ends thereof. Handles are attached to the tubes for relative rotation of the tubes and thereby effect cutting by the cutting edges. The cutting edges are circular and overlap each other for shearing cutting action upon rotation.

16 Claims, 2 Drawing Sheets

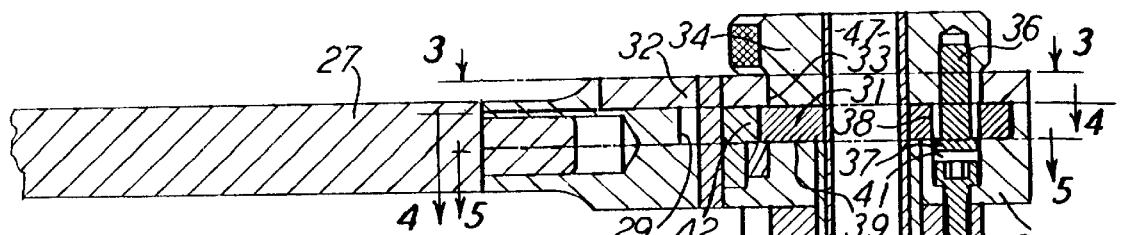
FIG. 2
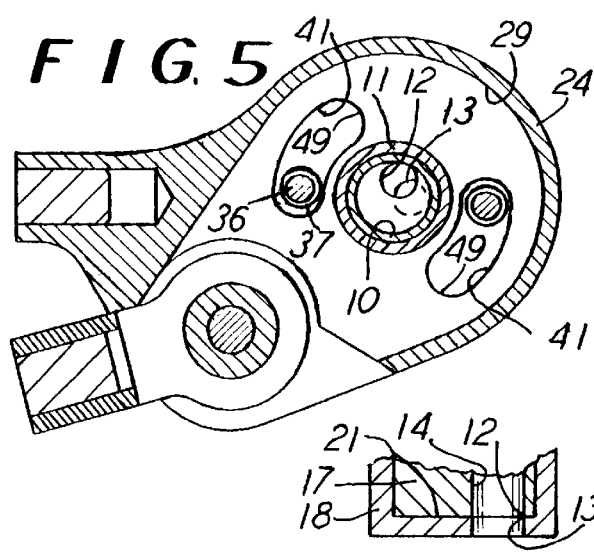
FIG. 5
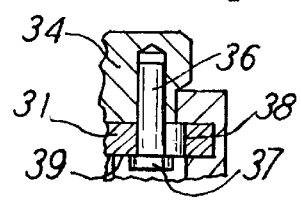
FIG. 6
FIG. 7
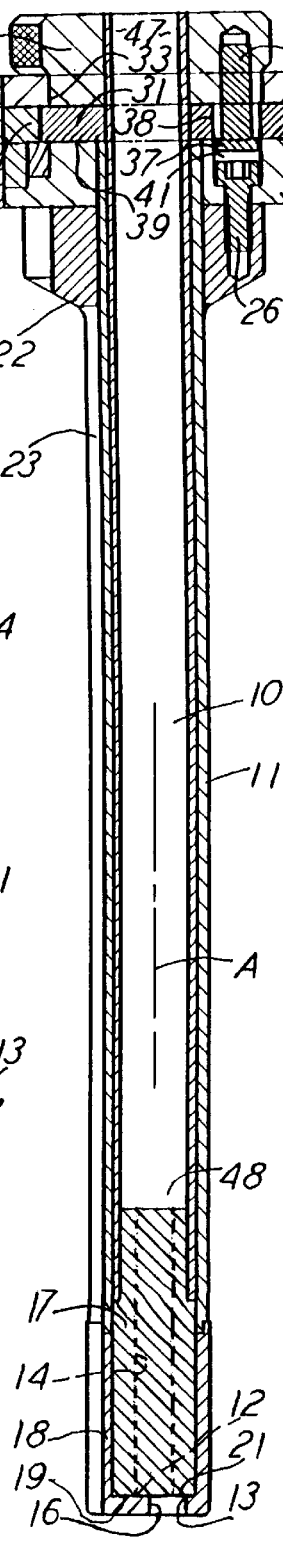

ROTARY CUTTER

This invention relates to a rotary cutter, and, more particularly, it is useful in surgical procedures where pins, wires, screws, or the like may be cut while on a patient's body.

BACKGROUND OF THE INVENTION

It is important in some instances to have a metal cutter which can cut at a location somewhat distant or remote from the handle portion of the cutter, that is, the cutting edges are located remote from the handles. With that arrangement, the cutting edges can be positioned at the very sight where the item to be cut is located.

Further, the cutter of this invention is arranged for cutting elongated objects, such as surgical pins and the like, and to do so in a shearing action and at the optimum location on the item to be cut, such as at the very base where the item protrudes from its support.

Still further, it is important in this invention to have a rotary cutter which is narrow in its extent at the position of the cutting edges themselves, and thus the cutter can be utilized for remote cutting and it can be positioned in narrow openings to the location of the item to be cut.

Also, the cutter of this invention operates in a shear cutting action, and the two cutting edges performing the shearing are held in close proximity to each other for accurate and precision cutting. Still further, the cutter is arranged to be highly leveraged in a mechanical advantage arrangement whereby the operator can maneuver handles of the cutter for easy cutting of metal objects.

Still further, the cutter of this invention is arranged so that the cutting edges can be readily and easily positioned on the item to be cut, and thus the cutting edges are initially set in a receptive position and are then maneuvered, such as by cutter handles, to where the cutting edges will perform the shearing action desired.

In this accomplishment, the item to be cut can be a fastener, such as a pin, screw, or the like, and it can protrude beyond its fastening functional length, but, nevertheless, the cutter of this invention will engage the protruding fastener and cut it at a base location relative to the body which is being held by the fastener.

This invention provides a rotary cutter constructed of telescoping tubular members which are arranged with cutting edges disposed at the remote end of the cutter. A workpiece can be engaged by the remote end of the cutter, and, upon cutting the workpiece, the cut portion is trapped in the tubular members for later removal.

BRIEF DESCRIPTION OF THE DRAWINGS

FIG. 2 is a sectional view taken substantially along the jagged line designated 2—2 in FIG. 1.

FIGS. 3, 4, and 5 are sectional views taken along the respective lines 3—3 and 4—4 and 5—5 of FIG. 2.

FIG. 6 is a sectional view similar to a portion of FIG. 2 but showing the parts in different positions.

FIG. 7 is an enlarged view of the lower end of FIG. 2 with parts in different positions.

DETAILED DESCRIPTION OF THE PREFERRED EMBODIMENT

Figure 1:
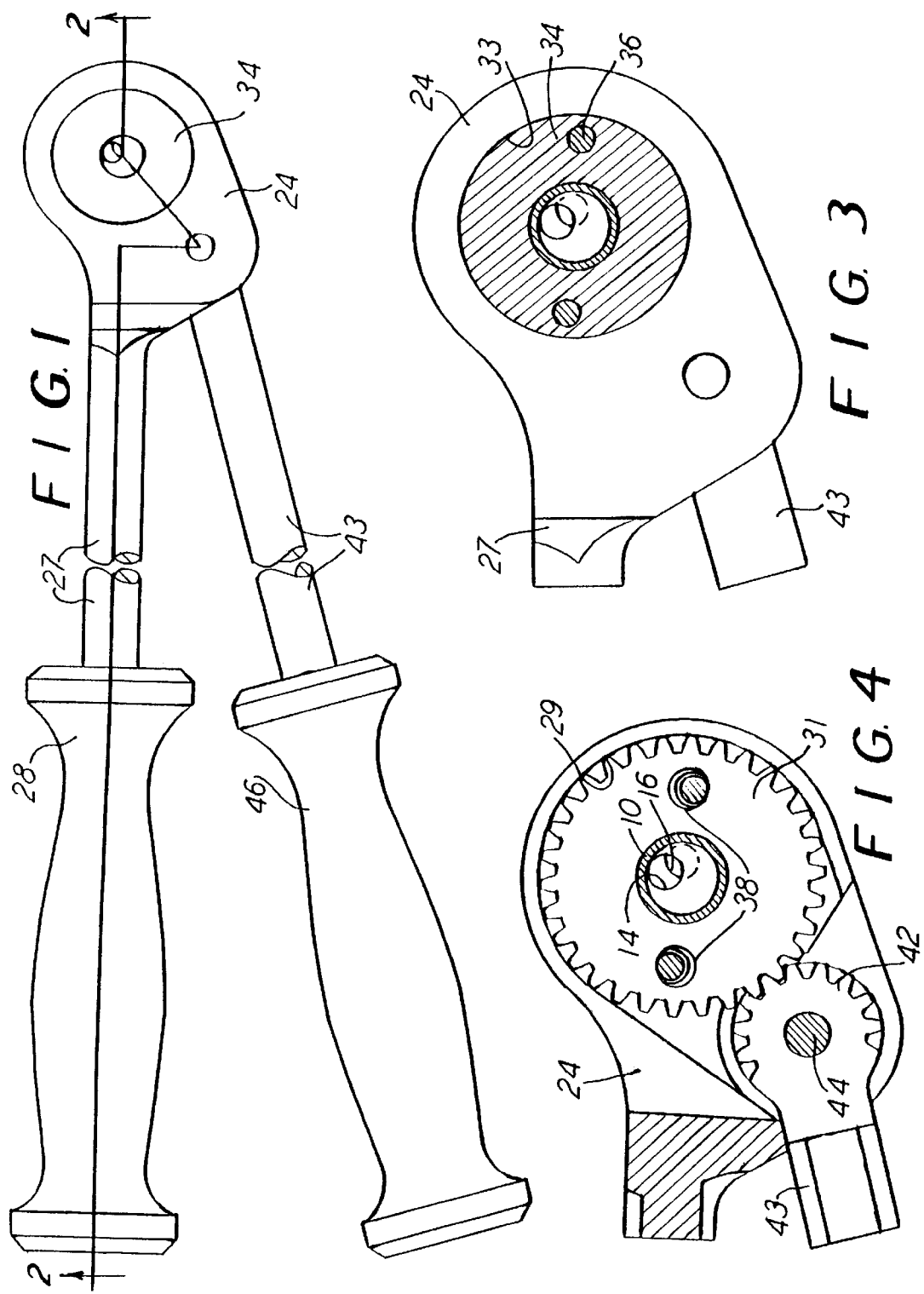
FIG. 1 is a top plan view of an embodiment of a cutter of this invention, with the handles shown foreshortened.

The essence of the invention is the arrangement of two tubular members 10 and 11 which are telescoped together in snug relationship, as seen in FIG. 2. The members 10 and 11 are substantially coextensive along their longitudinal axes, and the upper ends thereof are subject to the operational forces, and the lower ends provide the respective cutting edges 12 and 13. The tubes 10 and 11, being snugly telescoped together, are rotatable relative to each other such that the cutting edges 12 and 13 can pass each other in the cutting action and thereby shear the workpiece or item to be cut when the workpiece extends through openings 14 and 16 which define the respective cutting edges 12 and 13. The edges 12 and 13 are disposed in complete circles, and they are respectively offset from the longitudinal axis A of the tubes 10 and 11, and they are also disposed so that they can be axially aligned with each other for reception of the workpiece which can then extend into the circular openings 13 and 16 prior to moving the cutting edges 12 and 13 to their relative offset positions for the cutting action mentioned. The tube 10 has an elongated cylindrical piece 17 incorporated therein and presenting the elongated cylindrical opening 14. The piece 17 is affixed with the remainder of the tube 10 so that they both always rotate in unison. The outward tube 11 has a cylindrical piece 18 affixed thereto and snugly telescoped with the piece 17. There is an end wall 19 on the shown lower end of the piece 18, and that wall is of course transverse to the longitudinal axis A. It is that transverse wall 19 which has the opening 16 and thus presents the circular cutting edge 13, as described above.

The arrangement is such that the pieces 17 and 18 are in tight sliding contact at the juncture 21, and thus the shearing action with the cutting edges 12 and 13 will always be in sliding contact with each other for optimum shearing relationship in the cutting operation. Likewise, the rotating mechanism, on the upper end of FIG. 2 and to be described later, also is arranged to assure that the surfaces. 19 and 21 remain in tight sliding contact relative to each other when the members 10 and 11 are rotated.

There is a block or base piece 22 which lends support to the tubes 10 and 11, and there may be an extension 23. A body 24 is attached to the base 22 by means of screws 26 extending therebetween. The body 24 has a handle 27 affixed thereto and projecting therefrom for use by the operator as one of the handles of the tool. There is of course a grip 28 on the handle 27 which is rigidly connected to the body 24. The body 24 has an upwardly facing cavity 29, and a circular gear 31 is disposed in the cavity 29, such as seen in FIGS. 2 and 4. The gear 31 is centered on the axis A. A cap 32 extends over both the body 24 and the gear 31, and it can be welded to the body 24 at the peripheral juncture therebetween. The cap 32 has a central opening 33, and a knob 34 extends into the opening 33 and is rotatable therein and it carries two pins 36 which hold the cap on and which are positioned to have heads 37 at the lower ends thereof, as seen in FIGS. 2 and 6. The shanks of the pins 36 extend through enlarged openings 38 in the gear 31, and thus the pin heads 37 are positioned in alignment with the lower surface 39 of the gear 31 to effect the assembly.

The tube 10 and the knob 34 and its pins 36 are arranged to form an initial sub-assembly, such as by welding them together. Thus, the orbital movement of the pins 36 about the axis A will cause rotation of the knob 34 and likewise rotation of the tube 10 about the axis A. That rotation is created by rotation of the gear 31 which engages the pins 36. It will be noted that the body 24 has arcuate slots 41 for reception of the pin heads 37 and thus permitting the oscillating movement of the pins 36 in the two slots 41.

As mentioned, the gear 31 has two holes 38 which are of a diametrical size slightly greater than the pin heads 37 which can therefore pass downwardly through the holes 38 and into the arcuate slots 41, as shown. Next, clockwise rotation of the knob 34 will cause the pin heads 37 to move slightly in the openings 38 and to the position underneath the lower surface 39 of the gear 31, and thus trap the pins 36 relative to the gear 31 and thereby hold the welded assembly of the knob 34 and the tube 10 and the pins 36 in strict axial confinement. FIG. 7 shows the pin heads 37 in their desired trapped positions.

Rotation of the gear 31 is created by another gear 42 formed on the end of a handle 43 which is pivotal on a pin 44 extending through the body 24, and which is in mesh with the gear 31. Again, the handle 43 has a hand grip 46, and it will be seen and understood that upon movement of the handle 43 the gear 42 is rotated, and, being in mesh with the gear 31, the gear 31 is rotated to thereby rotate the tube 10 and move the cutting edge 12 relative to the cutting edge 13. Initial movement of the handle 43, such as away from the handle 27, will cause the circular cutting edges 14 and 16 to align with each other, such as apparent from the FIGS. 3, 4, and 5.

Next, movement of the handle 43 toward the handle 47 will cause the cutting edge 12 to become offset relative to the edge 13, and thus produce the shearing action desired for cutting a workpiece extending within the circular openings 14 and 16.

In that cutting action, the cylindrical opening 14 will have moved beyond alignment with the opening 16 and it will thus close off the cylindrical interior of the tube 10 and thereby present a closed pocket 48 for receiving and holding the cut portion of the item which was previously extending through both openings 14 and 16. In that regard, this cutter is useful for cutting and locations distant from the handles 27 and 43, and to retain the cut portion of the workpiece in the interior of the tube 10. Also, it will be seen that the upper end 47 of the tube 10 is cylindrically open, and thus the cut portion of the workpiece can be retrieved through the end 47.

It will thus be seen that this cutter is narrow in its girth through the diameter of the tube 11, and thus it can be utilized in remote positions with only limited access openings to the work site such as in surgical procedures within a person's body. Also, with the two-gear and handle arrangement, there is considerable mechanical force advantage in this cutter. Further, when the cutter is placed in the open handle position, and that may be when the pin heads 37 abut the respective ends 49 of the arcuate slots 41, then the cutting cylinders 14 and 15 are aligned for ease of reception of the workpiece to be cut. Still further, with the cutting edges 12 and 13 being circular in their shapes, they need not fully pass beyond each other to achieve the full shear cut, but, by virtue of the circular configuration, they can be placed in the relative positions seen in FIGS. 3, 4, and 5 to achieve full cut of a workpiece which is of an adequate cross-sectional size at least slightly beyond that indicated by the overlapping showings of those drawings.

In the open position mentioned, the ends 49 of the arcuate slots 41 serve as stops for the pin heads 37, to achieve the initial alignment mentioned. Also, the planar end 21 of the tube 10 presents a wall, along with the aforementioned wall 19 of the tube 11, such as the two members present those walls on planes transverse to the axis A and define their respective cutting edges 12 and 13 on those walls. The overlapping lower wall 19 provides for the snug relationship between the cutting edges 12 and 13, as mentioned, and that is also in conjunction with the pin heads 37 which are trapped relative to the gear 31 to thus assure the tight sliding and shearing action between the cutting edges 12 and 13, while the gear 31 is held down by the welded-on cap 32.

What is claimed is:

1. A rotary cutter comprising two tubular members snugly telescopically inter-related and having a longitudinal axis extending along the tubular length of said members and with each of said members terminating in an end disposed adjacent to each other, a wall on each of said members respectively disposed at each of said ends and in overlapping relationship to each other and lying along respective planes which are transverse to said axis, each of said walls having a cutting edge thereon arranged to be in shearing cutting relationship with each other, a force-advantage mechanism connected with said members for rotating said members relative to each other and in opposite directions of rotation about said axis, and said cutting edges on said members being arranged to move past each other during the rotation of said members to thereby shear a work-piece disposed between said cutting edges.

2. The rotary cutter as claimed in claim 1, wherein said cutting edges are disposed to be offset relative to said axis and relative to each other, in the cutting positions of said edges, and said cutting edges are disposed to be alignable relative to each other prior to the cutting.

3. The rotary cutter as claimed in claim 1, wherein said walls have openings therein which define said cutting edges, and said openings are offset from said axis for rotating past each other upon rotation of said members in the cutting action.

4. The rotary cutter as claimed in claim 1, including said members having shoulders in contact with each other on the respective said members for restricting movement of said members relative to each other along said axis.

5. The rotary cutter as claimed in claim 1, wherein said force-advantage mechanism consists of a handle connected with each respective said member for the rotation of said members and with said handles extending along a common plane, and said members are elongated to position said cutting edges on a plane parallel to and remote from said handles.

6. The rotary cutter as claimed in claim 1, wherein said walls have circular openings therein which contain said cutting edges, and said openings being located on respective ones of said members to be positioned in axial alignment with each other in one position of rotation of said members, and to be offset from each other in another position of rotation of said members.

7. The rotary cutter as claimed in claim 6, including a stop operatively associated with said members and being arranged to limit rotation of said members relative to each other and thereby have said members rotated to a position where said openings are in axial alignment for reception of a work piece to be cut.

8. The rotary cutter as claimed in claim 1, wherein said force-advantage mechanism includes handles disposed at a leverage-connected position relative to said members, and said force-advantage mechanism includes a fulcrum-type inter-connection between said members and said handles for additional leverage between said handles and said members.

9. A rotary cutter comprising two tubular members snugly telescopically inter-related and having a centrally-disposed longitudinal axis extending along the tubular length of said members and with each of said members terminating in an end disposed adjacent to each other, a wall on each of said members respectively disposed at each of said ends and in overlapping relationship to each other and lying along respective planes which are parallel to each other and are transverse to said axis, each of said walls having a cutting edge thereon disposed eccentric to said axis and arranged to move past each other upon rotation of said members and to thereby be in shearing cutting relationship with each other, a handle connected with each of said members, and a gear-tooth rotation drive connected with one of said handles and one of said members for mechanical force-advantage in the rotation of said one of said members.

10. The rotary cutter as claimed in claim 9, wherein each of said cuttng edges is in the shape of circle.

11. The rotary cutter as claimed in claim 10, wherein each said circle has a central axis which is parallel to said axis of said members.

12. The rotary cutter as claimed in claim 11, including a stop operatively associated with said members and being arranged to limit rotation of said members relative to each other and thereby have said members rotated to the position where said circles are in axial alignment for reception of a work piece to be cut.

13. The rotary cutter as claimed in claim 9, including shoulders on each of said members and facing in the direction of said axis for restricting axial movement of said members relative to each other.

14. The rotary cutter as claimed in claim 9, wherein said tubular members are hollow tubes which receive a portion of a work piece, and said walls are disposed and arranged to form a pocket with said tubes whereby upon shearing action on a work piece disposed within said tubes a portion of the work piece is trapped within said pocket.

15. The rotary cutter as claimed in claim 14, wherein said tubes are open at the ends thereof opposite said ends with said walls, for the removal of the portion of the work piece trapped within said tubes.

16. The rotary cutter as claimed in claim 15, wherein each of said cutting edges is in the shape of a circle which has a central axis parallel to said axis of said members, and said circles are both eccentric to the respective said tubes and arranged to be axially aligned with each other in a first position of relative rotation of said tubes and to be offset relative to each other in a second position of relative rotation of said tubes.

* * * * *